United States Patent [19]

Cottman

[11] 4,446,264

[45] May 1, 1984

[54] SYNERGISTIC ANTIOXIDANT MIXTURES

[75] Inventor: Kirkwood S. Cottman, Akron, Ohio

[73] Assignee: The Goodyear Tire & Rubber Company, Akron, Ohio

[21] Appl. No.: 368,604

[22] Filed: Apr. 15, 1982

[51] Int. Cl.$^3$ ............... C07C 153/07; C07C 153/09; C08K 5/37

[52] U.S. Cl. ................... 524/109; 524/112; 524/282; 524/283; 524/289; 524/302; 549/252; 549/253; 560/15; 560/17; 560/144; 560/152; 560/154; 260/455 R

[58] Field of Search ............ 549/252, 253; 560/15, 560/17, 144, 152, 154; 524/112, 109, 282, 283, 289, 302; 528/293; 562/426; 260/455 R

[56] References Cited

U.S. PATENT DOCUMENTS

| | | | |
|---|---|---|---|
| 2,397,960 | 4/1946 | Gribbins | 562/426 |
| 2,561,673 | 7/1951 | Proell et al. | 562/426 |
| 2,581,514 | 1/1952 | Chilcote | 460/154 |
| 3,078,290 | 2/1963 | Hechenbleikner et al. | 524/302 |
| 3,340,236 | 9/1967 | Greenlee et al. | 528/293 |
| 3,535,368 | 10/1970 | Steinberg | 560/15 |
| 3,637,809 | 1/1972 | Kleiner | 560/15 |
| 3,716,466 | 2/1973 | Hook | 560/154 |

FOREIGN PATENT DOCUMENTS

| | | |
|---|---|---|
| 2251448 | 4/1973 | Fed. Rep. of Germany . |
| 2810521 | 10/1978 | Fed. Rep. of Germany . |

OTHER PUBLICATIONS

Gerald Scott: *Atmospheric Oxidation and Antioxidants*, (1965), pp. 188 to 209, 217, 219, 253–257, 262–273, 290–299.

*Primary Examiner*—Veronica P. Hoke
*Attorney, Agent, or Firm*—D. O. Nickey

[57] ABSTRACT

Compounds prepared by reacting maleic anhydride, maleic acid or their esters with thiols; which exhibit a synergistic effect when combined with a phenolic antioxidant in the stabilization of organic materials such as natural and synthetic polymers, rubbers, lubricants and oil, etc. are disclosed.

16 Claims, No Drawings

SYNERGISTIC ANTIOXIDANT MIXTURES

TECHNICAL FIELD

This invention relates to antioxidant systems. More particularly, it relates to organic compositions stabilized against oxidative degradation by a two component system consisting of a novel compound and at least one antioxidant.

BACKGROUND ART

It is well-known that such organic materials as plastics, rubbers, lubricating oils, etc. are prone to oxidation and deterioration in the presence of oxygen. Oxidation of organic materials causes the loss of those intrinsic properties characteristic of the organic material. With a view to preventing deterioration a variety of antioxidants have been developed, however, these antioxidants fail to prevent completely to deterioration of the desired properties of the materials to which they are added. Thus, those skilled in the art are constantly searching for new and more effective antioxidant systems which are useful for the protection of polymers and other organic materials.

Antioxidant synergists have been known in the art for sometime. For example, U.S. Pat. No. 3,492,336 discloses a novel tetra-alkyl thioethyl thiodisuccinate compound for use with phenolic type antioxidants in the stabilization of polyolefins.

An antioxidant composition comprising a synergistic mixture of a phenol, an amine and a sulfone is described in U.S. Pat. No. 3,839,210. Specifically, U.S. Pat. No. 3,839,210 discloses an antioxidant composition comprised of a mixture of an oil soluble phenol, an oil soluble amine and a long chain alkylthioethyl sulfone compound in an oxidizable organic material, particularly petroleum oils.

In addition, U.S. Pat. No. 3,758,549 discloses polyalkanol esters of alkylthio-alkanoic acids as synergists with phenolic antioxidants and U.S. Pat. Nos. 3,666,716 and 3,505,225 disclose derivatives of diphenylamine and the phenylnaphthylamines as synergists with dialkyl 3,3'-thiodipropionates.

The art of using a combination of antioxidants has already been put into practice in industry and such anti-oxidant combinations are often highly effective. The applicant has prepared a variety of compounds which have been examined with a view towards obtaining more stable organic compositions. As a result it has been found that the combined use of the novel compounds of this invention with phenolic antioxidants brings about an unexpectedly powerful antioxidative effect. None of the above cited patents or other literature in the art has disclosed or even suggests the compounds or antioxidant systems which are used in the practice of this invention.

DISCLOSURE OF THE INVENTION

The present invention relates to a stable organic composition which is prepared by mixing an organic material with at least one compound expressed by the general formulae I through VII:

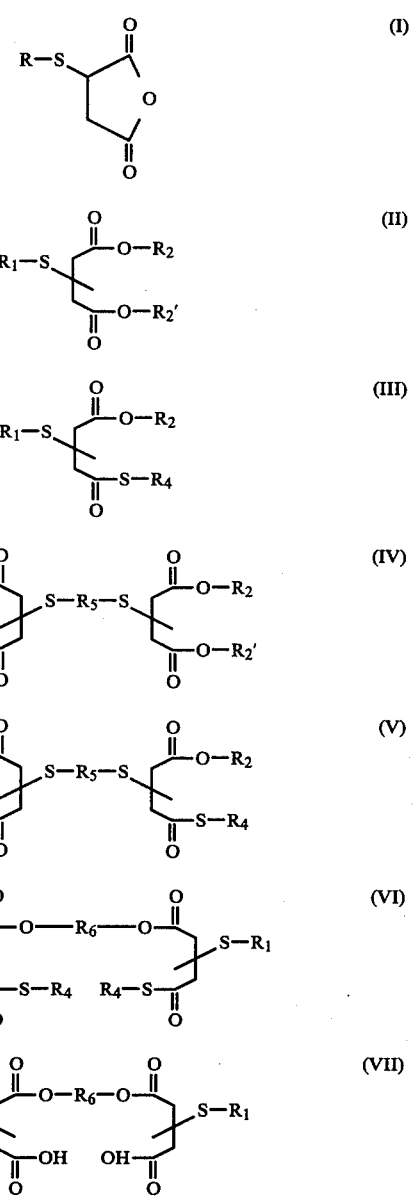

wherein R is selected from the group comprising alkyl of 1 to 20 carbon atoms, aralkyl of 7 to 10 carbon atoms, phenyl and; $R_1$ is selected from the group comprising alkyl of 1 to 20 carbon atoms, aralkyl of 7 to 10 carbon atoms and phenyl; $R'_2$ is selected from the group comprising, alkyl of 1 to 20 carbon atoms and a radical of the formula:

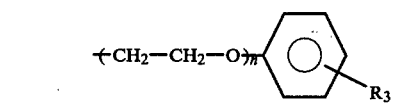

wherein n is a real number from 1 to 30 and $R_3$ is hydrogen or an alkyl radical of 1 to 12 carbon atoms; $R_2$ is selected from the group of $R'_2$ and hydrogen; and $R_4$ is an alkyl radical of 1 to 20 carbon atoms; and $R_5$ is an alkylene radical of 2 to 10 carbon atoms or the radical:

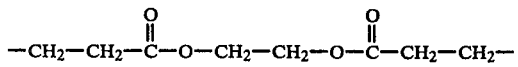

and $R_6$ is a radical selected from the group comprising alkylene of 2 to 10 carbon atoms and a radical of the formula:

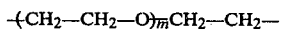

wherein m is O or a real number from 1 to 10; together with at least one phenolic antioxidant.

The present invention also relates to a stable organic composition which is prepared by mixing an organic material with the reaction product of a compound of structural formula VII and a reactant of the structural formula "A":

$$OH-(CH_2-CH_2-O)_pH \quad \text{"A"}$$

wherein p is a real number from 1 to 10; and $R_1$ and $R_6$ are defined as above; together with at least one phenolic antioxidant.

In addition, the present invention relates to a stable organic composition which is prepared by mixing an organic material with the reaction product of a compound of structure formula VII and a reactant of structural formula "B":

$$Q-OH \quad \text{"B"}$$

wherein Q is an alkyl radical of 1 to 20 carbon atoms or a radical of the formula:

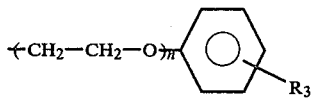

wherein n is a real number from 1 to 20 and $R_3$ is hydrogen or an alkyl radical of 1 to 12 carbon atoms; and wherein $R_1$ and $R_6$ are defined as above; together with at least one phenolic antioxidant.

The present invention also relates to the compounds expressed by general formulae I to VII, the reaction product of compound VII and reactant "A", and the reaction product of compound VII and reactant "B".

The compounds of this invention exhibit their novel properties when combined with the variety of stabilizers known as phenolics.

DETAILED DESCRIPTION OF INVENTION

Typical of the phenolic antioxidants with stabilizing properties that are improved by the addition of compounds of the present invention are phenolic compounds having the general formulae:

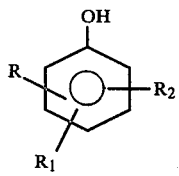

wherein R is a tert. alkyl radical having 4 to 8 carbon atoms, a cycloalkyl radical having 5 to 12 carbon atoms, or an aralkyl radical having 7 to 12 carbon atoms, and wherein $R_1$ and $R_2$ are alkyl radicals having 1 to 12 carbon atoms, cycloalkyl radicals having 5 to 12 carbon atoms, or aralkyl radicals having from 7 to 12 carbon atoms; or the formula:

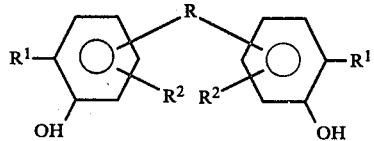

wherein R is an alkylidine radical having 1 to 4 carbon atoms, the group —O—, or the group —S—, and wherein $R^1$ and $R^2$ are alkyl radicals having 1 to 12 carbon atoms, cycloalkyl radicals having 5 to 12 carbon atoms, or aralkyl radicals having 7 to 12 carbon atoms. Preferably at least one of $R^1$ and $R^2$ is a tert.alkyl radical having 4 to 8 carbon atoms and is in a position ortho to the hydroxyl group: or the formula:

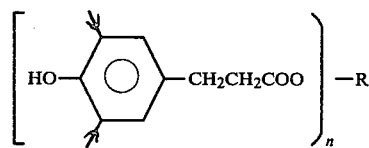

wherein $\psi$ is a tert.butyl radical and wherein n is an integer from 1 to 4 and R is an alkyl radical having 1 to 20 carbon atoms, an alkylene radical having 2 to 6 carbon atoms, a thiodialkylene radical wherein each alkylene radical has 2 to 6 carbon atoms, a trivalent radical derived from a straight or branched chain hydrocarbon having 3 to 8 carbon atoms, or a tetravalent radical derived from a straight or branched chain hydrocarbon having 4 to 8 carbon atoms.

Typical phenolic antioxidants applicable in the present invention include:
2,6-di-tert.butyl-4-methylphenol
2,4,6-tri-tert.butylphenol
2,2'-methylene-bis-(4-methyl-6-tert.butylphenol)
2,2'-thio-bis-(4-methyl-6-tert.butylphenol)
4,4'-thio-bis-(3-methyl-6-tert.butylphenol)
4,4'-butylidene-bis-(6-tert.butyl-3-methylphenol)
Styrenated phenol
Butylated Octylated Phenol
Butylated α-methylstyrenated phenol
Styrenated butylated m, p-cresol
4,4'-methylenebis (2,6-di-tert.butylphenol)
2,2'-methylenebis[4-methyl-6-(1-methylcyclohexyl)-phenol]
Butylated reaction product of p-cresol and dicyclopentadiene
Tetrakis[methylene 3-(3,5-di-tert.butyl-4-hydroxyphenyl)propionate]methane
1,3,5-trimethyl-2,4,6-tris(3,5-di-tert.butyl-4-hydroxybenzyl)benzene
Thiodiethylene bis[3-(3,5-di-tert.butyl-4-hydroxyphenyl)propionate]
Octadecyl 3-(3,5-di-tert.butyl-4-hydroxyphenyl)propionate These formulae represent the major families of presently known phenolic antioxidants. The various R substituents are given to generally describe the substituents that can be placed on the phenolic compounds. The compounds of the present invention have demonstrated synergistic activity with phenolic antioxidants and the structural formulae are intended to be illustrative and not limiting.

The compounds of the present invention will also exhibit synergistic activity with a class of antioxidants known as polymerizable antioxidants. These antioxidants have shown great potential in the stabilization of oxidizable organic materials due to their non-extractability and non-volatility. These antioxidants as monomers, with phenolic functional groups, are polymerized with one or more comonomers so as to have the antioxidant moiety chemically attached to the polymer structure.

These polymerizable phenolic antioxidants are known in the art and are covered by numerous U.S. patents.

The materials that may be protected by the antioxidant system described herein are oxidizable vulcanized and unvulcanized polymers susceptible to oxidative degradation, such as natural rubber, balata, gutta percha and oxidizable synthetic polymers, including those containing carbon to carbon double bonds, such as rubbery diene polymers, both conjugated and nonconjugated. Representative examples of the synthetic polymers used in the practice of this invention are polychloroprene; homopolymers of a conjugated 1,3-diene such as isoprene and butadiene, and in particular, polyisoprenes and polybutadienes having essentially all of their repeat units combined in a cis-1,4 structure; copolymers of a conjugated 1,3-diene such as isoprene and butadiene with up to 50 percent by weight of at least one copolymerizable monomer including ethylenically unsaturated monomers such as styrene and acrylonitrile; butyl rubber, which is a polymerization product of a major proportion of a monoolefin and a minor proportion of a multiolefin such as butadiene or isoprene; polyurethanes containing carbon to carbon double bonds; and polymers and copolymers of monoolefins containing little or no unsaturation, such as polyethylene, polypropylene, ethylene propylene copolymers and terpolymers of ethylene, propylene and a nonconjugated diene such as dicyclopentadiene, 1,4-hexadiene, ethylidene norbornene and methylene norbornene. Other protectable materials include oils and polyesters.

The compounds of the present invention have as one of their characteristic properties the ability to improve the effect of numerous compounds which are presently used as antioxidants for organic materials. Thus, while the compounds of the present invention may be considered as stabilizers in their own right, their properties are such that they would be more conventionally classified as "synergists", in that, when combined with known phenolic stabilizers they exhibit the ability to increase stabilization to a degree far exceeding that which would be expected from the additive properties of the individual components.

The compounds represented by the general formulae I through VII and the reaction product of compounds VII and reaction "A" and compound VII and reaction "B" may comprise from 10 to 90 percent of the antioxidant system, however, the maximum effectiveness of the antioxidant system is generally achieved when a compound of the present invention is combined with an antioxidant at ratios from 1:4 to 4:1. The optimum ratio of a given combination varies depending upon the organic material to which it is added.

The antioxidant system according to the present invention can be added to said organic materials in various ways. For instance, it can be applied either after dilution with a solvent or directly as it is. Addition of the present antioxidant system to the organic material can be performed either by applying a mixture prepared in advance or by applying these ingredients individually. Mixing of the present antioxidant system with substances such as resins, plastics and rubbers, which are solid at room temperatures can be readily performed by means of conventional equipment, such as mixers, kneaders and roll mills.

It has been found that addition of the antioxidant system of this invention to organic materials in the range from 0.02 to 10.0 parts per hundred of organic material by weight will effectively protect the organic material from deterioration.

As described above the antioxidant system according to the present invention comprises the novel compounds expressed herein combined with at least one phenolic antioxidant. The antioxidant system of the present invention demonstrates antioxidant activities superior to that of most conventional systems prepared by combining two or more commercial antioxidants.

Best Mode For Carrying Out The Invention

The novel compounds of this invention may be prepared in a number of ways, that is, the order of incorporating the various functional groups is not usually critical. For example, in preparing compounds of structural formula II, one may react dioctylmaleate with dodecane thiol to form dioctyl-2-(dodecylthio) succinate. Another method for synthesizing the same product is to react maleic anhydride or maleic acid with dodecanethiol. This would give 2-(dodecylthio)succinic anhydride and 2-(dodecylthio) succinic acid, respectively. Either of these products may be reacted with an alcohol, for example, octyl alcohol, to give dioctyl-2-(dodecylthio) succinate.

Thiols, such as $R_1$—SH and H—$SR_5$SH, are reacted with either maleic anhydride, maleic acid, fumaric acid or an ester thereof using an inert solvent or no solvent at all. Representative of suitable inert solvents are toluene, benzene, chlorobenzene, alkanes and chlorinated alkanes, xylene, and tetrahydrofuran. Basic catalysts, such as sodium hydroxide, potassium hydroxide and benzyl-trimethylammonium hydroxide may be used to catalyze the reaction. Temperatures for incorporating $R_1$—SH or H—$SR_5$SH may range from room temperature or below to the boiling point of the reactant. Atmospheric pressure is normally adequate although pressures above one atmosphere should not hinder the reaction.

Alkylthioester functions, such as an in structural formulae III, V, and VI are incorporated by reacting a mercaptan, $R_4$SH, with an anhydride within the scope of the present invention. Alcohols within the scope of the present invention, such as $R_2$OH, and H—O—$R_6$OH may be reacted with anhydrides, such as 2-(dodecylthio)succinic anhydride to give predominately a product, such as octyl-2-(dodecylthio)hydrogen succinate. If at least two moles of octanol is used in the presence of an acid catalyst, one will produce dioctyl-2-(dodecylthio) succinate.

Representative of the acid catalysts that can be used for the esterification are sulfuric acid, methane sulfonic acid, toluene sulfonic acid, acidified resins, acidified clays and the like. Solvents are not needed for the esterification reaction but inert solvents, such as benzene, toluene and xylene may be used. The esterification reaction may be run under vacuum or at atmospheric pressure or under slightly superatmospheric pressure. It is preferred to remove the water by-product during the esterification reaction. The following examples are presented for illustration and not limitation.

EXAMPLE 1

Preparation of 2-(dodecylthio)-succinic anhydride

Compound of Structural Formula (I)

A three-neck flask fitted with a thermometer, agitator and water condenser was charged with 101 grams of n-dodecanethiol, 50 ml of tetrahydrofuran, 50 grams of maleic anhydride and 10 drops of Triton B TM. The reaction was heated to 80°–90° C. and agitated until all of the dodecanethiol had reacted. The volatiles were distilled off, product weight was 151 grams. It was verified by N.M.R. to be 2-(dodecylthio)-succinic anhydride.

EXAMPLE 2

Preparation of 2-(dodecylthio)-succinic acid

Compound of Structural Formula (II)

The procedure of Example 1 was followed except that 66 gm of maleic anhydride was used in place of 50 gm of maleic anhydride. The product was washed with water and the resulting diacid had a melting point of 93°–95° C., and the reaction product was determined to be 2-(dodecylthio)-succinic acid.

EXAMPLE 3

Preparation of mono-n-dodecanethiol ester of 2 or 3-(dodecylthio)-succinic acid

Compound of Structural Formula (III)

To a three-neck flask fitted with a thermometer, agitator and water condenser was charged 50 grams of maleic anhydride and 101 grams of dodecanethiol, 25 ml. of xylene, and 10 drops of Triton B TM. The mixture was reacted at 90° C. for 2½ hours to make the product of Example 1. Then 101 grams more of dodecanethiol was added along with 6 pellets of KOH. The flask contents were reacted at 130° C. to 140° C. until the thiol had all reacted. The volatiles were distilled off to a pot temperature of 160° C. at 20 mm. of mercury. The weight of the product was 247 grams. The product was determined to be the mono-n-dodecanethiol ester of 2 or 3-(dodecylthio)-succinic acid.

EXAMPLE 4

Preparation of Tetra-n-octyl 2,2'-(trimethylenethio)-bis succinate

Compound of Structural Formula IV

To the reaction vessel described in Example 1 was added 50 grams of dioctylmaleate, 7 grams of 1,3-dimercaptopropane and 5 grams of Triton B TM. The reaction mixture was heated to 65° C. for 3½ hours. The product had no odor and the yield of tetra-n-octyl 2,2'-(trimethylenedithio)bis succinate was theoretical.

EXAMPLE 5

Preparation of Tetra-n-octyl 2,2'-[ethylenebis(oxycarbonyl ethylenethio)]-bis succinate Compound of Structural Formula V To the reaction vessel described in Example 1 was added 40 grams of dioctylmaleate, 14 grams of glycol dimercaptopropionate, 26 drops of Triton B TM and 50 ml of toluene. The reaction mixture was heated at 70° C. for 16 hours. The volatiles were distilled off and the product was characterized by NMR analysis to be tetra-n-octyl 2,2'-[ethylenebis(oxycarbonyl ethylenethio)]-bis succinate.

EXAMPLE 6

Preparation of Compound of Structural Formula VI

Twenty-seven grams of maleic anhydride and 101 grams of dodecanethiol were reacted in the presence of 5 grams of tetrahydrofuran, 5 drops of Triton B TM, and 3 pellets of KOH at 90° C. for one hour in the reaction vessel described in Example 1. The mixture was then reacted at 130°–155° C. for an additional 2½ hours to form the same product described in Example 3. Then 18 grams of triethylene glycol, 36 drops of methanesulfonic acid and 100 mls of toluene were added. The mixture was refluxed to azeotrope off the water formed and then the volatiles were distilled off to yield a product with a weight of 134 grams.

EXAMPLE 7

Preparation of Compound of Structural Formula VII

Seventy-four grams of the product prepared as described in Example 1 is added to the reaction vessel described in Example 1 along with 150 ml of toluene, and 37 gm of triethyleneglycol. The reaction mixture is refluxed for 11 hours to remove the water of reaction. The volatiles are removed under vacuum to obtain the product.

EXAMPLE 8

Preparation of a Compound of Structural Formula I

Wherein R is the Radical

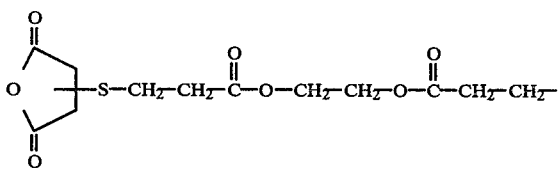

To the reaction vessel described in Example 1 was added eighty grams of glycoldimercaptopropionate, 67 grams of maleic anhydride, 6 drops of Triton B TM and 5 mls. of tetrahydrofuran. The reaction mixture was heated at 90° C. for 3½ hours. The viscous solution was diluted with 40 ml more of tetrahydrofuran and 40 ml of toluene and then reacted at 70° C. for one hour longer. The volatiles were distilled off and the product weight was 147 grams.

EXAMPLE 9

Preparation of Dioctyl 2-(dodecylthio)-succinate

Compound of Structural Formula II

To the reaction vessel described in Example 1 was added 50 gm of dioctylmaleate, 5 drops of Triton B ™ and 31½ grams of n-dodecanethiol. Reaction mixture was heated to 70° C. for one hour. The volatiles were then distilled off and the product was characterized by NMR analysis to be dioctyl 2-(dodecylthio)-succinate. The yield was 100 percent of theory.

EXAMPLE 10

Preparation of a Compound of Structural Formula II

To the reaction vessel described in Example 1, 25 gm of a product prepared as described in Example 1 was added along with 75 ml of toluene, 0.5 gram of toluene sulfonic acid and 84 gm of Igepal CO-520 (a product manufactured by GAF, Inc.) known to be nonylphenoxypoly(ethyleneoxy) ethanol, containing 50 percent ethylene oxide. The reaction mixture was refluxed for 4.5 hours to remove the water of reaction. The reaction product was then neutralized with 5 grams of dry $Na_2CO_3$ and filtered. The volatiles were removed under a vacuum and the product weight was determined to be 108 grams.

EXAMPLE 11

Preparation of a Compound of Structural Formula II

Wherein $R_2$ is the Radical

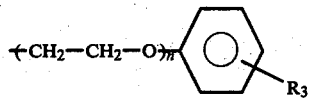

Twenty-seven grams of the product prepared in Example 1 is added to 75 ml of toluene, 12 drops of toluene sulfonic acid and 84 grams of Igepal CO-520. The reaction mixture is refluxed for four hours to remove the water of reaction. The product is then neutralized with 5 grams of $Na_2CO_3$ and filtered. The volatiles are stripped off to yield the product.

EXAMPLE 12

Preparation of Monododecylthio Ester of Succinic Acid

To the reaction vessel described in Example 1 was added 25 grams of succinic anhydride, 52 grams of dodecanethiol, 6 pellets of KOH and 40 ml xylene. The reaction mixture was heated to 140° C. until all the dodecanethiol had reacted. The reaction mixture was distilled to remove volatiles and 70 grams of an off-white product remained. NMR analysis determined the product to be mono-dodecylthiol ester of succinic acid.

EXAMPLE 13

Preparation of the Reaction Product of Structural Formula VII and Reactant "A"

To the reaction vessel described in Example 1 is added 150 gms of the product from Example I, 100 mls. toluene and 22.5 grams of 1,4-butanediol. The reaction mixture is refluxed for 2 hours and then 0.5 grams of toluenesulfonic acid and 37.5 grams of triethylene glycol is added. The reaction mixture is refluxed until the water of reaction is removed and then the desired product is isolated.

EXAMPLE 14

Preparation of the Reaction Product of Structural Formula VII and Reactant "B"

To the reaction vessel described in Example 1 is added 150 grams of the product from Example 1 and 22.5 grams of 1,4-butanediol. The reaction mixture is heated to 110° C. for 2 hours with stirring. Then 220 grams of Igepal CO-510, 1.0 grams of methanesulfonic acid and 125 mls. of toluene are added to the reaction vessel and refluxed until the theoretical amount of $H_2O$ has been azeotroped off.

Testing of Compounds

The antioxidative activity of the compounds and mixtures of this invention will be demonstrated by means of the oxygen absorption test. The testing procedure is of the type described in detail in *Industrial and Engineering Chemistry*, Vol. 43, Page 456, (1951), and *Industrial and Engineering Chemistry*, Volume 45, Page 392 (1953).

Synergism is exhibited when a combination is more active than an equal amount of each component used separately. That is, synergism is evident when a combination of a phenolic antioxidant and a synergist is more active than an equal amount of the phenolic antioxidant or synergist used separately.

Compounds within the scope of the present invention were evaluated as synergists with a commercially accepted phenolic antioxidant, known as Wingstay ™ C (product of The Goodyear Tire & Rubber Company which is the reaction product of phenol, α-methylstyrene and isobutylene).

A total of 1 part per hundred of the antioxidant system was added to 100 parts of SBR 1006 and aged at 100° C. until 1% $O_2$ was absorbed by weight. The ratio of Wingstay ™ C to test compounds in the antioxidant system ranged from 0 to 100 percent in 25 percent increments.

The following Tables set out the compounds tested, the antioxidant system ratio, and the hours to absorb 1 percent $O_2$.

TABLE I

Oxygen Absorption of SBR-1006 at 100° C.
Compound From Example 1, 2-(dodecylthio)succinic Anhydride
Compound of Structural Formula I

| Parts Test Compound Parts/Hundred | Parts Wingstay C Parts/Hundred | Hours to Absorb 1% $O_2$ |
|---|---|---|
| 0 | 1.00 | 237 |
| .25 | .75 | 535 |
| .50 | .50 | 480 |
| .75 | .25 | 245 |
| 1.00 | 0 | 53 |

TABLE II

Oxygen Absorption of Compound of Structural Formula II
Compound From Example 9

| Parts Test Compound Parts/Hundred | Parts Wingstay C Parts/Hundred | Hours to Absorb 1% $O_2$ |
|---|---|---|
| 0 | 1.0 | 226 |
| .25 | .75 | 322 |
| .50 | .50 | 387 |
| .75 | .25 | 226 |
| 1.0 | 0 | 32 |

TABLE III

Compound of Structural Formula III
Compound from Example 3

| Parts Test Compound Parts/Hundred | Parts Wingstay C Parts/Hundred | Hours to Absorb 1% $O_2$ |
|---|---|---|
| 1.0 | 0 | 48 |
| .75 | .25 | 297 |
| .50 | .50 | 506 |
| .25 | .75 | 532 |
| 0 | 1.0 | 237 |

TABLE IV

Compound of Structural Formula IV
Compound From Example 4

| Parts Test Compound Parts/Hundred | Parts Wingstay C Parts/Hundred | Hours to Absorb 1% $O_2$ |
|---|---|---|
| 1.0 | 0 | 10 |
| .75 | .25 | 88 |
| .50 | .50 | 203 |
| .25 | .75 | 298 |
| 0 | 1.0 | 251 |

TABLE V

Compound of Structural Formula VI
Compound From Example 6

| Parts Test Compound Parts/Hundred | Parts Wingstay C Parts/Hundred | Hours to Absorb 1% $O_2$ |
|---|---|---|
| 0 | 1.0 | 248 |
| .25 | .75 | 470 |
| .50 | .50 | 434 |
| .75 | .25 | 233 |
| 1.0 | 0 | 45 |

TABLE VI

Compound Prepared By Reacting Structural Formula VII With Reactant "A" Wherein 1 Mole of the Reaction Product From Example 1 Is Reacted With 1 Mole of Triethylene Glycol In The Presence Of An Acid

| Parts Test Compound Parts/Hundred | Parts Wingstay C Parts/Hundred | Hours to Absorb 1% $O_2$ |
|---|---|---|
| 1.0 | 0 | 31 |
| .75 | .25 | 286 |
| .50 | .50 | 428 |
| .25 | .75 | 410 |
| 0 | 1.0 | 226 |

Polypropylene Testing

The antioxidant systems of the present invention were also evaluated in polypropylene. The testing procedure consists of dissolving the compound or compounds in a suitable solvent such as toluene. The solution was deposited on a commercially available unstabilized polypropylene known as Profax ™ 6501 at a concentration of 0.10 pph by weight if evaluated alone and at a concentration of 0.05 pph by weight when evaluated with a phenolic antioxidant. The materials were blended with a Henschel blender until all the solvent had evaporated. The stabilized resin was then injection molded to form a dumbell shaped test specimen using appropriate injection molding conditions.

The resulting test specimens were then oven aged in triplicate at 140° C. in a circulating hot air oven and observed daily. The first signs of degradation that were noted is crazing. The failure point was embrittlement to flexing, that is, bending by hand to less than 90°. Failure times are the average for the three samples.

Seven compounds of the present invention were compared with Plastanox ™ LTDP (dilaurylithiodipropionate) and Plastanox ™ STDP (distearylthiodipropionate) as secondary antioxidants or synergists for polypropylene. Irganox 1010 served as the primary phenolic antioxidant and has the structural formula:

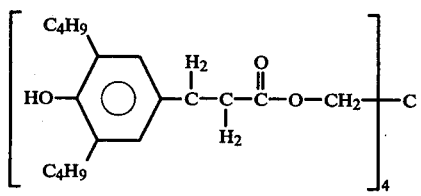

The samples were prepared as described above and exposed in a Fade-O-Meter to determine their ultra violet light discoloration resistance. Much of the data in the following Tables is in the form of color readings from a Gardner Color Instrument. All are in the standard Rd, a, b notation, however, there is an added value indicated as ΔE. ΔE is based on the L, a, b, notation and is the linear distance from standard white (L=100, a=0, b=0). ΔE is calculated as follows:

$$\Delta E = (100 - \text{sample})^2 + (a, \text{sample})^2 + (b_1 \text{sample})^2$$

Thus, ΔE, is a single number representation of lightness-darkness without taking into account hue. The protection afforded by the antioxidant system of the present invention was determined by oven aging the samples till failure. In the following Tables the composition of the test samples is in parts per hundred by weight unless otherwise noted.

POLYPROPYLENE TEST TABLES

| Component | #1 | #2 | #3A | #3B | #4A | #4B | #5A |
|---|---|---|---|---|---|---|---|
| Profax 6501 | 100.0 | → | → | → | → | → | → |
| Irganox 1010 | 0.10 | 0.05 | 0 | 0.05 | 0 | 0.05 | 0 |
| Cmpd from Example #9 | 0 | 0 | 0.10 | 0.05 | 0 | 0 | 0 |
| Cmpd from Example 5 | | | | 0 | 0.10 | 0.05 | 0 |
| Cmpd which is the 1:1 Reaction Product of Example 1 Product and Triethylene Glycol | | | | | | | 0.10 |
| Original | | | | | | | |
| Rd | 48.6 | 48.7 | 48.7 | 48.5 | 47.5 | 52.0 | 48.3 |
| a | −1.4 | −1.5 | −1.4 | −1.4 | −1.2 | −1.1 | −1.4 |
| b | +3.7 | +3.4 | +2.2 | +3.0 | +1.5 | +3.4 | +4.0 |
| $\Delta_E$ | 30.6 | 30.4 | 30.4 | 30.5 | 31.1 | 28.1 | 30.8 |
| Oven Aged 1 Day @ 140° C. | | | | | | | |
| Rd | 44.1 | 46.6 | 45.7 | 46.0 | 47.3 | 49.5 | failed |
| a | −1.2 | −1.2 | −1.2 | −1.2 | −1.3 | −1.1 | failed |
| b | +5.1 | +4.5 | +3.4 | +3.2 | +4.6 | +3.5 | failed |
| $\Delta_E$ | 34.0 | 32.1 | 32.6 | 32.4 | 31.6 | 29.9 | failed |
| Oven Aged 5 Days @ 140° C. | | | | | | | |
| Rd | 44.2 | 46.5 | 46.0 | 47.5 | 47.7 | 49.3 | failed |
| a | −1.2 | −1.5 | −1.6 | −1.4 | −1.8 | −1.3 | failed |
| b | +7.4 | +5.5 | +8.1 | +4.6 | +7.2 | +4.9 | failed |
| $\Delta_E$ | 34.3 | 32.3 | 33.2 | 31.5 | 31.8 | 30.2 | failed |
| Oven Aged 10 Days @ 140° C. | | | | | | | |
| Rd | 34.3 | 41.9 | failed | 41.7 | failed | 43.2 | failed |
| a | −1.3 | −1.7 | failed | −1.5 | failed | −1.5 | failed |

POLYPROPYLENE TEST TABLES -continued

| | | | | | | |
|---|---|---|---|---|---|---|
| b | +10.5 | +6.4 | failed | +5.7 | failed | +6.2 failed |
| $\Delta_E$ | 35.3 | 31.3 | failed | 31.9 | failed | 30.5 failed |

Fade-O-Meter Exposed 200 hours

| | | | | | | |
|---|---|---|---|---|---|---|
| Rd | 50.6 | 54.8 | 45.0 | 51.6 | 43.3 | 49.0 47.3 |
| a | −1.7 | −1.7 | −1.4 | −1.8 | −0.6 | −1.6 −1.2 |
| b | +7.7 | +5.2 | +14.1 | +6.1 | +17.3 | +14.6 +14.1 |
| $\Delta_E$ | 29.9 | 26.6 | 35.7 | 28.9 | 38.1 | 33.3 34.2 |

Oven Aged Till Failure @ 140° C., Days

| | | | | | | |
|---|---|---|---|---|---|---|
| Craze | 81 | 54 | 6 | 81 | 6 | 97 1 |
| Destruction | 81 | 55 | 6 | 82 | 6 | 97 1 |

Test Samples

| Components | #5B | #6A | #6B | #7A | #7B |
|---|---|---|---|---|---|
| Profax 6501 | 100.0 | → | → | → | → |
| Irganox 1010 | 0.05 | 0 | 0.05 | 0 | 0.05 |
| Cmpd which is the 1:1 Reaction Product of Example 1 Product and Triethylene Glycol | 0.05 | 0 | 0 | 0 | 0 |
| Compound From Example 4 | 0 | 0.10 | 0.05 | 0 | 0 |
| Compound of Structural Formula VI | | | | 0.10 | 0.05 |

Original

| | | | | | |
|---|---|---|---|---|---|
| Rd | 49.2 | 48.8 | 50.0 | 47.3 | 48.0 |
| a | −1.4 | −1.3 | −1.3 | −1.8 | −1.4 |
| b | +3.1 | +2.1 | +2.9 | +5.9 | +4.3 |
| $\Delta_E$ | 30.1 | 30.3 | 29.5 | 31.8 | 31.0 |

Oven Aged 1 Day @ 140° C.

| | | | | | |
|---|---|---|---|---|---|
| Rd | 47.8 | 48.9 | 48.9 | 46.9 | 46.3 |
| a | −1.4 | −1.3 | −1.1 | −1.3 | −1.3 |
| b | +4.5 | +2.9 | +3.4 | +9.3 | +4.9 |
| $\Delta_E$ | 31.2 | 30.3 | 30.3 | 33.4 | 32.4 |

Oven Aged 5 Days @ 140° C.

| | | | | | |
|---|---|---|---|---|---|
| Rd | 47.6 | 46.4 | 49.5 | 43.9 | 48.1 |
| a | −1.8 | −1.8 | −1.4 | −1.7 | −1.5 |
| b | +6.3 | +6.7 | +5.0 | +13.5 | +5.8 |
| $\Delta_E$ | 31.7 | 32.6 | 30.2 | 36.3 | 31.2 |

Oven Aged 10 Days @ 140° C.

| | | | | | |
|---|---|---|---|---|---|
| Rd | 46.9 | failed | 47.3 | failed | 47.1 |
| a | −2.0 | failed | −1.7 | failed | −1.7 |
| b | +8.1 | failed | +6.2 | failed | +7.1 |
| $\Delta_E$ | 32.5 | failed | 31.9 | failed | 32.1 |

Fade-O-Meter Exposed 200 Hours

| | | | | | |
|---|---|---|---|---|---|
| Rd | 53.5 | 47.6 | 49.9 | 38.9 | 43.6 |
| a | −2.2 | −0.8 | −1.8 | +0.5 | −0.7 |
| b | +14.4 | +23.0 | +9.4 | +19.5 | +17.6 |
| $\Delta_E$ | 30.7 | 38.4 | 30.8 | 42.0 | 38.0 |

Oven Aged Till Failure @ 140° C.

| | | | | | |
|---|---|---|---|---|---|
| Craze | 87 | 5 | 91 | 6 | 94 |
| Destruction | 88 | 5 | 91 | 6 | 94 |

Test Sample

| Component | #8A | #8B | #9A | #9B | #10A | #10B |
|---|---|---|---|---|---|---|
| Profax 6501 | 100.0 | → | → | → | → | → |
| Irganox 1010 | 0 | 0.05 | 0 | 0.05 | 0 | 0.05 |
| Compound of Structural Formula #1, Example 8 | 0.10 | 0.05 | 0 | 0 | 0 | 0 |
| Plastanox LTDP | | | 0.10 | 0.05 | | |
| Plastanox STDP | | | | | 0.10 | 0.05 |

Original

| | | | | | | |
|---|---|---|---|---|---|---|
| Rd | 44.1 | 47.0 | 49.5 | 50.4 | 48.1 | 48.2 |
| a | −1.7 | −1.4 | −1.2 | −1.2 | −1.3 | −1.3 |
| b | +8.9 | +6.9 | +2.3 | +2.7 | +2.1 | +4.1 |
| $\Delta_E$ | 34.8 | 32.2 | 29.8 | 29.2 | 30.7 | 30.9 |

Oven Aged 1 Day @ 140° C.

| | | | | | | |
|---|---|---|---|---|---|---|
| Rd | 36.6 | 39.6 | 48.7 | 48.2 | 49.7 | 48.0 |
| a | −0.1 | −0.6 | −1.1 | −1.1 | −1.2 | −1.3 |
| b | +14.5 | +11.0 | +2.8 | +2.9 | +2.5 | +3.4 |
| $\Delta_E$ | 41.9 | 38.6 | 30.4 | 30.7 | 29.6 | 31.0 |

Oven Aged 5 Days @ 140° C.

POLYPROPYLENE TEST TABLES -continued

| | | | | | | |
|---|---|---|---|---|---|---|
| Rd | 30.4 | 37.7 | 48.4 | 49.2 | 47.7 | 46.8 |
| a | +2.1 | +0.1 | −1.5 | −1.4 | −1.6 | −1.5 |
| b | +17.7 | +13.9 | +4.4 | +4.0 | +4.7 | +4.4 |
| $\Delta_E$ | 47.9 | 40.8 | 30.8 | 30.2 | 31.4 | 32.0 |

Oven Aged 10 Days @ 140° C.

| | | | | | | |
|---|---|---|---|---|---|---|
| Rd | Failed | 34.4 | 45.2 | 48.3 | 44.2 | 46.7 |
| a | Failed | +0.6 | −2.0 | −1.5 | −2.0 | −1.6 |
| b | Failed | +15.9 | +9.0 | +5.1 | +11.3 | +6.3 |
| $\Delta_E$ | Failed | 44.0 | 34.0 | 31.1 | 35.3 | 32.3 |

Fade-O-Meter Exposed 200 Hours

| | | | | | | |
|---|---|---|---|---|---|---|
| Rd | 22.2 | 40.4 | 43.7 | 50.3 | 50.3 | 54.2 |
| a | +11.8 | +1.0 | −0.8 | −1.9 | −1.9 | −2.0 |
| b | +24.4 | +22.0 | +16.0 | +11.9 | +15.8 | +10.8 |
| $\Delta_E$ | 58.1 | 42.2 | 37.3 | 31.5 | 33.3 | 28.7 |

Oven Aged Till Failure @ 140° C.

| | | | | | | |
|---|---|---|---|---|---|---|
| Craze | 7 | 91 | 16 | 98 | 12 | 99 |
| Destruction | 8 | 91 | 16 | 98 | 13 | 100 |

All of the compounds of the present invention tested demonstrated synergistic effects with the phenolic antioxidant Irganox 1010 in polypropylene. On a cost effectiveness basis the synergists of the present invention are superior to those presently in the market place.

Generally, all of the systems, except the compound from Example 8 provided excellent thermal discoloration resistance and where superior to Irganox 1010 alone. Since the systems of the present invention were not individually optimized, it is not possible to predict which synergist is the most effective, however, all the compounds of the present do function as synergists.

COMPARATIVE EXAMPLE

Compound From Example 12

A compound of the structural formula

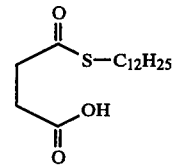

was synthesized and evaluated as a synergist with the commercially accepted phenolic antioxidant known as Wingstay C ™ (product of The Goodyear Tire & Rubber Company, which is the reaction product of phenol, α-methylstyrene and isobutylene) in SBR 1006.

A total of 1 part per hundred of the antioxidant system was added to 100 parts of SBR 1006 and aged at 100° C. until 1% $O_2$ was absorbed by weight.

| Parts Test Compound | Wingstay C ™ | Hours to 1% $O_2$ |
|---|---|---|
| 1.0 | 0 | 6 |
| 0 | 1.0 | 252 |
| 0.5 | 0.5 | 211 |

The data indicates that the compounds of the present invention must be substituted in at least one position "α" to the carbonyl groups

by an alkyl thiol group for synergistic activity to be present.

Industrial Applicability

From the testing data obtained it is evident that the compounds disclosed herein significantly enhance the stability of SBR 1006 and polypropylene when combined with a known antioxidants.

The industrial applications are readily apparent in light of the synergistic activity of these novel compounds when used in conjunction with known phenolic antioxidants. Use of the compounds of this invention would significantly reduce the amount of costly phenolic antioxidant that is needed to provide the desired stability of the organic material. In addition, the use of these novel antioxidant systems could lessen the undesirable effects of color formation and discoloration.

While certain representative embodiments and details have been shown for the purpose of illustrating the invention, it will be apparent to those skilled in this art that various changes and modifications may be made herein without departing from the spirit or scope of this invention.

I claim:

1. A composition of matter which comprises an organic material prepared by reacting maleic anhydride, maleic acid or their esters with thiols; said organic material being defined by one of the following structural formulae:

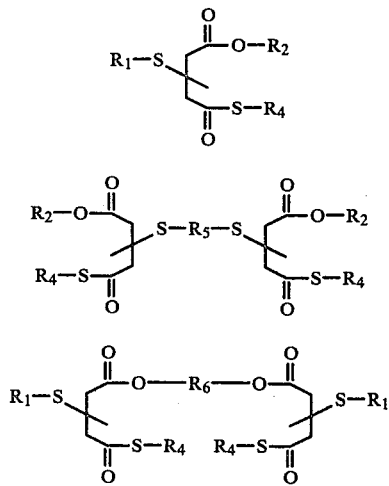

wherein $R_1$ is selected from the group comprising alkyl of 1 to 20 carbon atoms, aralkyl of 7 to 10 carbon atoms, and phenyl; $R_2$ is hydrogen or a radical of the formula:

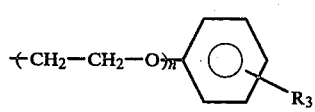

wherein n is a real number from 1 to 30 and $R_3$ is hydrogen or an alkyl radical of 1 to 12 carbon atoms; $R_4$ is an alkyl radical of 1 to 20 carbon atoms; $R_5$ is an alkylene radical of 2 to 10 carbon atoms or the radical of the formula:

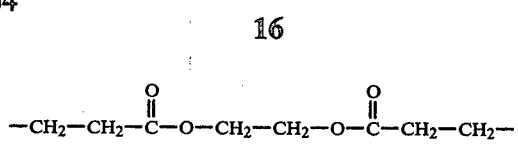

and $R_6$ is a radical selected from the group comprising alkylene of 2 to 10 carbon atoms and a radical of the formula:

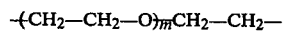

wherein n is 0 or a real number from 1 to 10.

2. A composition of matter comprising an organic material prepared by reacting a compound of the structural formula VII:

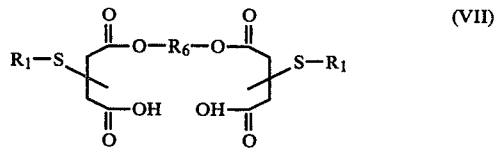 (VII)

and a reactant of structural Formula "A"

$$OH-CH_2-CH_2-O)_pH \qquad \text{"A"}$$

wherein p is a real number from 1 to 10; and $R_1$ is selected from the group comprising alkyl of 1 to 20 carbon atoms, aralkyl of 7 to 10 carbon atoms and phenyl; and wherein $R_6$ is a radical selected from the group comprising alkylene of 2 to 10 carbon atoms and a radical of the formula:

wherein m is 0 or a real number from 1 to 10.

3. A composition of matter comprising an organic material prepared by reacting a compound of structural formula VII:

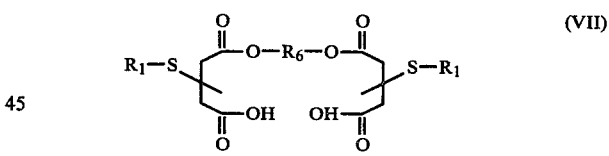 (VII)

and a reactant of the formula "B"

$$Q-OH \qquad \text{"B"}$$

wherein Q is an alkyl radical of 1 to 20 carbon atoms or a radical of the formula:

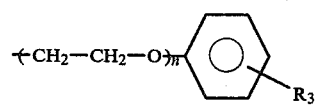

wherein n is a real number from 1 to 20 and $R_3$ is hydrogen or an alkyl radical of 1 to 12 carbon atoms; and wherein $R_1$ is selected from the group comprising alkyl of 1 to 20 carbon atoms, aralkyl of 7 to 10 carbon atoms and phenyl, and wherein $R_6$ is a radical selected from the group comprising alkylene of 2 to 10 carbon atoms and a radical of the formula:

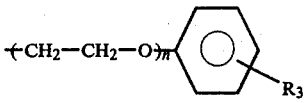

wherein m is 0 or a real number of 1 to 10.

4. A stable organic composition which is prepared by mixing an organic material selected from the group consisting of natural and synthetic polymers and oils with at least one compound expressed by the general formulae I through VII:

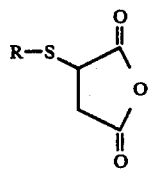 (I)

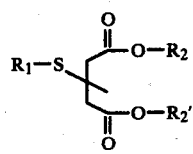 (II)

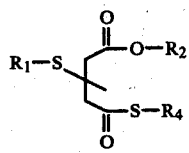 (III)

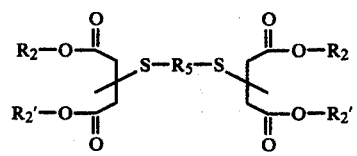 (IV)

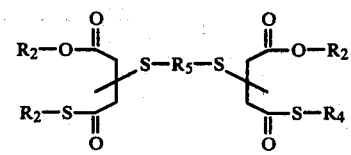 (V)

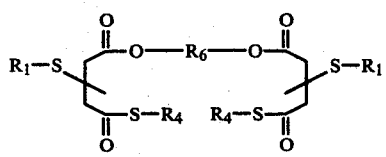 (VI)

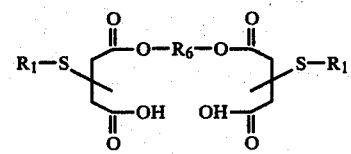 (VII)

wherein R is selected from the group comprising alkyl of 1 to 20 carbon atoms, aralkyl of 7 to 10 carbon atoms, phenyl; and $R_1$ is selected from the group comprising alkyl of 1 to 20 carbon atoms, aralkyl of 7 to 10 carbon atoms and phenyl; $R'_2$ is selected from the group comprising alkyl of 1 to 20 carbon atoms and a radical of the formula:

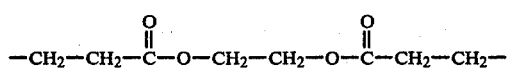

wherein n is a real number from 1 to 30 and $R_3$ is hydrogen or an alkyl radical of 1 to 12 carbon atoms; $R_2$ is selected from the group of $R'_2$ and hydrogen; and $R_4$ is an alkyl radical of 1 to 20 carbon atoms; and $R_5$ is an alkylene radical of 2 to 10 carbon atoms or the radical:

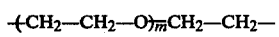

and $R_6$ is a radical selected from the group comprising alkylene of 2 to 10 carbon atoms and a radical of the formula:

$-(CH_2-CH_2-O)_{\overline{m}}CH_2-CH_2-$ wherein m is 0 or a real number from 1 to 10; together with at least one phenolic antioxidant.

5. A stable organic composition according to claim 4 wherein R is an alkyl radical of 4 to 12 carbon atoms.

6. A stable organic composition which is prepared by mixing an organic material selected from the group consisting of natural and synthetic polymers and oils with the reaction product of a compound of the structural formula VII:

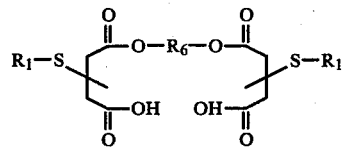 (VII)

and a reactant of structural formula "A":

$OH-(CH_2-CH_2-O)_{\overline{p}}H$ "A"

wherein p is a real number from 1 to 10; and $R_1$ is selected from the group comprising alkyl of 1 to 20 carbon atoms, aralkyl of 7 to 10 carbon atoms and phenyl; and wherein $R_6$ is a radical selected from the group comprising alkylene of 2 to 10 carbon atoms and a radical of the formula:

$-(CH_2-CH_2-O)_{\overline{m}}CH_2-CH_2-$ wherein m is 0 or a real number from 1 to 10; together with at least one phenolic antioxidant.

7. A stable organic composition which is prepared by mixing an organic material selected from the group consisting of natural and synthetic polymers and oils with the reaction product of a compound of structural formula VII and a reactant of the formula "B":

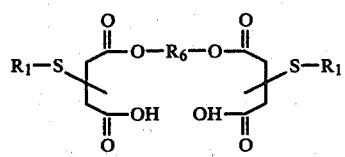 (VII)

Q—OH wherein Q is an alkyl radical of 1 to 20 carbon atoms or a radical of the formula:

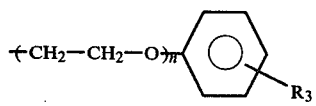

wherein n is a real number from 1 to 20 and $R_3$ is hydrogen or an alkyl radical of 1 to 12 carbon atoms; and wherein $R_1$ is selected from the group comprising alkyl of 1 to 20 carbon atoms, aralkyl of 7 to 10 carbon atoms and phenyl, and wherein $R_6$ is a radical selected from the group comprising alkylene of 2 to 10 carbon atoms and a radical of the formula:

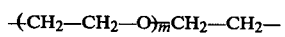

wherein m is 0 or a real number of 1 to 10; together with at least one phenolic antioxidant.

8. A stable organic composition according to claim 4, 6, or 4 wherein the phenolic antioxidant is selected from the group comprising:
2,6-di-tert.butyl-4-methylphenol
2,4,6-tri-tert.butylphenol
2,2'-methylene-bis-(4-methyl-6-tert.butylphenol)
2,2'-thio-bis-(4-methyl-6-tert.butylphenol)
4,4'-thio-bis-(3-methyl-6-tett.butylphenol)
4,4'-butylidene-bis-(6-tert.butyl-3-methylphenol)
Styrenated phenol
Butylated Octylated Phenol
Butylated α-methylstyrenated phenol
Styrenated butylated m, p-cresol
4,4'-methylenebis (2,6-di-tert.butylphenol)
2,2'-methylenebis[4-methyl-6-(1-methylcyclohexyl)-phenol]
Butylated reaction product of p-cresol and dicyclopentadiene
Tetrakis[methylene 3-(3,5-di-tert.butyl-4-hydroxyphenyl)propionate]methane
1,3,5-trimethyl-2,4,6-tris(3,5-tert.butyl-4-hydroxybenzyl)benzene
Thiodiethylene bis[3-(3,5-di-tert.butyl-4-hydroxyphenyl)propionate]
Octadecyl 3-(3,5-di-tert.butyl-4-hydroxyphenyl) propionate 9. A stable organic material according to claims 4, 6 or 4 wherein the phenolic antioxidant is a polymerized phenolic monomer antioxidant.

10. A composition of claim 4 wherein the amount of said organic compound defined by structural formulae I through VII is 0.01 to 10 parts per hundred parts of said organic material.

11. A composition of claim 4 wherein said organic material is selected from poly mono-olefins and dienic polymers.

12. A composition of claim 4 wherein said organic material is selected from homopolymers and copolymers of alpha-mono-olefins and diene monomers.

13. A composition of claim 4 wherein said antioxidant composition comprises an organic compound of structural formulae I through VII and at least one phenolic antioxidant compound selected from hindered phenols, the combined amount of said organic compound and said other phenolic antioxidant compound being sufficient to produce a synergistic antioxidant effect.

14. A method for stabilizing an organic material selected from the group consisting of natural and synthetic polymers and oils comprising the addition of a compound according to structural formula III:

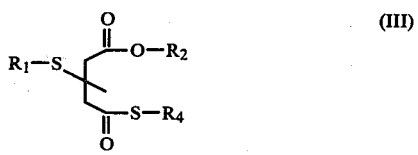

wherein $R_1$ is selected from the group comprising alkyl of 1 to 20 carbon atoms, aralkyl of 7 to 10 carbon atoms and phenyl; and $R_2$ is the same or different radical selected from the group comprising hydrogen, alkyl of 1 to 20 carbon atoms and a radical of a structural formula:

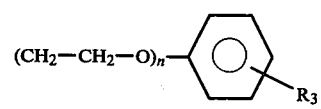

wherein n is a real number from 1 to 30; $R_3$ is hydrogen or an alkyl radical of 1 to 12 carbon atoms and at least one phenolic antioxidant.

15. A method for stabilizing an organic material selected from the group consisting of natural and synthetic polymers and oils comprising the addition of a compound according to structural formula I:

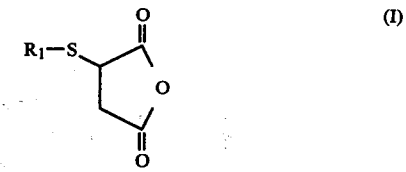

wherein R is selected from the group comprising alkyl of 1 to 20 carbon atoms, aralkyl of 7 to 10 carbon atoms and phenyl; together with at least one phenolic antioxidant to the organic material.

16. A method for stabilizing an organic material comprising the addition of a compound according to structural formula II:

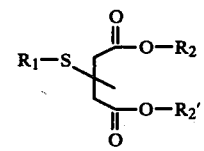

wherein $R_1$ is selected from the group comprising alkyl of 1 to 20 carbon atoms, aralkyl of 7 to 10 carbon atoms and phenyl; $R'_2$ is selected from the group comprising alkyl of 1 to 20 carbon atoms and a radical of the formula:

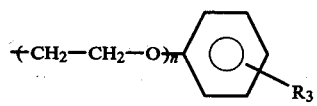

where in n is a real number from 1 to 20; $R_2$ is selected from the group of $R'_2$ and hydrogen; $R_3$ is hydrogen or an alkyl radical of 1 to 12 carbon atoms; and at least one phenolic antioxidant to the organic material.

* * * * *